United States Patent
Moaddeb et al.

(10) Patent No.: US 6,466,818 B1
(45) Date of Patent: Oct. 15, 2002

(54) POROUS IRRIGATED TIP ELECTRODE CATHETER

(75) Inventors: Shahram Moaddeb, Woodland Hills, CA (US); Michele M. Fung, Pasadena, CA (US); Gregory G. Brucker, Minneapolis, MN (US); Steven D. Savage, Paynesville, MN (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/371,905

(22) Filed: Aug. 10, 1999

Related U.S. Application Data
(60) Provisional application No. 60/116,195, filed on Jan. 15, 1999.

(51) Int. Cl.$^7$ .................................................. A61N 1/30
(52) U.S. Cl. .......................................... 604/21; 604/22
(58) Field of Search ...................... 604/19–22; 607/115, 607/116, 119, 120, 122, 123, 125, 129, 98–100, 112, 113, 148, 149, 153, 101; 606/41; 600/372, 373; 128/639, 642

(56) References Cited

U.S. PATENT DOCUMENTS

| | | | |
|---|---|---|---|
| 3,855,638 A | 12/1974 | Pilliar | 3/1 |
| 3,890,977 A | 6/1975 | Wilson | 128/418 |
| 4,101,984 A | 7/1978 | MacGregor | 3/1.5 |
| 4,167,607 A * | 9/1979 | De Nora et al. | 429/15 |
| 4,506,680 A | 3/1985 | Stokes | 128/786 |
| 4,934,381 A | 6/1990 | MacGregor | 128/784 |
| 4,984,581 A | 1/1991 | Stice | 128/772 |
| 5,209,734 A | 5/1993 | Hurley et al. | 604/158 |
| 5,269,752 A | 12/1993 | Bennett | 604/28 |
| 5,357,979 A | 10/1994 | Imran | 128/772 |
| 5,383,923 A | 1/1995 | Webster, Jr. | 607/125 |
| 5,462,521 A | 10/1995 | Brucker et al. | 604/20 |
| 5,643,197 A | 7/1997 | Brucker et al. | 604/20 |
| 5,681,344 A | 10/1997 | Kelly | 606/194 |
| 5,688,267 A | 11/1997 | Panescu et al. | 606/41 |
| 5,797,903 A | 8/1998 | Swanson et al. | 606/34 |
| 5,910,129 A | 6/1999 | Koblish et al. | 604/95 |
| 5,913,856 A * | 6/1999 | Chia et al. | 606/41 |
| 6,120,476 A | 9/2000 | Fung et al. | 604/95 |
| 6,171,275 B1 * | 1/2001 | Webster, Jr. | 604/20 |

FOREIGN PATENT DOCUMENTS

| EP | 0123456 | 10/1984 |
|---|---|---|

OTHER PUBLICATIONS

Application No. 09/371,438 (specification, claims and drawings) filed Aug. 10, 1999.
Amendment mailed Oct. 31, 2000 in Application No. 09/371,438.

* cited by examiner

*Primary Examiner*—Manuel Mendez
(74) *Attorney, Agent, or Firm*—Christie, Parker & Hale, LLP

(57) ABSTRACT

An irrigated tip catheter comprises a catheter body, a tip section, and a porous tip electrode. The catheter body has an outer wall, proximal and distal ends, and a lumen extending therethrough. The tip section comprises a segment of flexible tubing having proximal and distal ends and at least one lumen therethrough. The proximal end of the tip section is fixedly attached to the distal end of the catheter body. The porous tip electrode is fixedly attached to the distal end of the tubing of the tip section. The tip electrode has an outer surface and comprises a body and an insert. The body comprises a porous material through which fluid can pass and has a cavity therein. The insert, which comprises a non-porous material, is contained within the cavity of the shell. The insert has at least one passage extending therethrough in fluid communication with a lumen in the tip section. An infusion tube having proximal and distal ends extends through the central lumen in the catheter body. The distal end of the infusion tube is in fluid communication with the proximal end of the passage in the tip electrode, whereby fluid can flow through the infusion tube, into the passage in the tip electrode and through the porous material of tip electrode to the outer surface of the tip electrode.

41 Claims, 15 Drawing Sheets

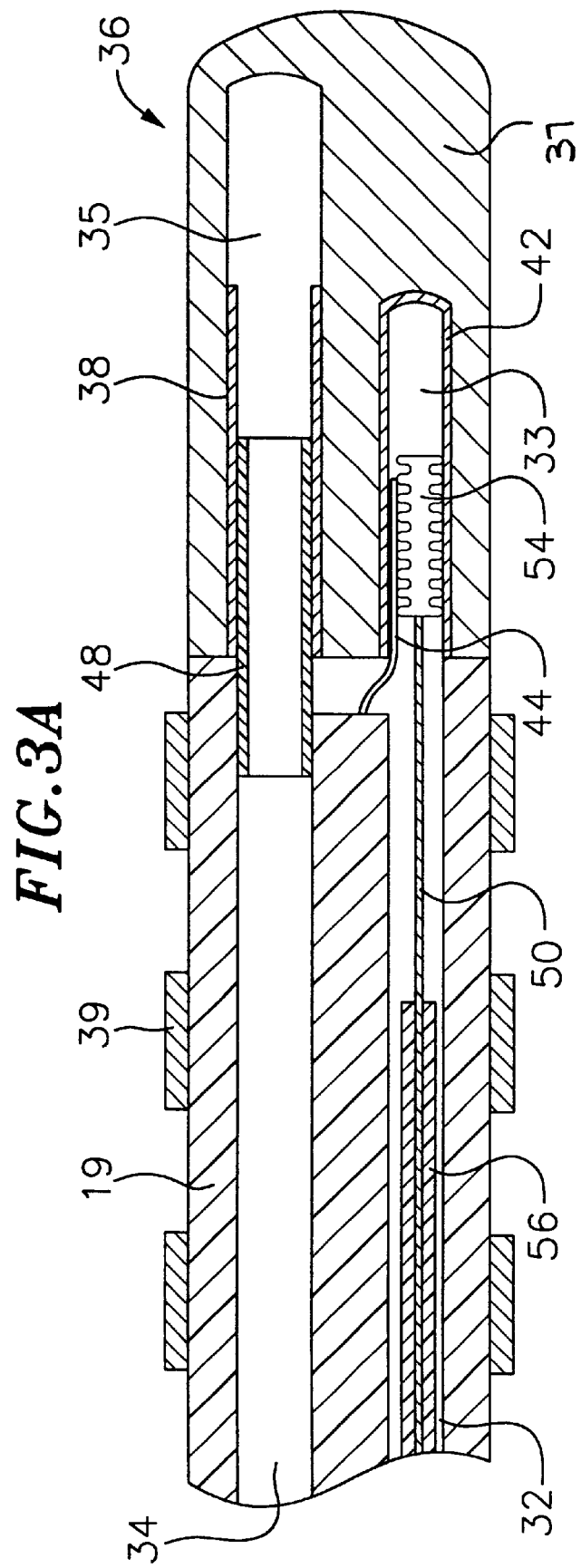

POROUS IRRIGATED TIP ELECTRODE CATHETER

CROSS-REFERENCE TO RELATED APPLICATION

This application is based on U.S. Provisional Application No. 60/116,195, filed Jan. 15, 1999, the disclosure of which is incorporated herein by reference.

FIELD OF THE INVENTION

The present invention is directed to an irrigated tip catheter, and more particularly to a porous tip electrode design for an irrigated tip catheter.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

In certain applications, it is desirable to have the ability to inject and/or withdraw fluid through the catheter. This is accomplished by means of an irrigated tip catheter. One such application is a cardiac ablation procedure for creating lesions which interrupt errant electrical pathways in the heart.

A typical ablation procedure involves the insertion of a catheter having a tip electrode at its distal end into a heart chamber. A reference electrode is provided, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60° C., a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

In a typical application of RF current to the endocardium, circulating blood provides some cooling of the ablation electrode. However, there is typically a stagnant area between the electrode and tissue which is susceptible to the formation of dehydrated proteins and coagulum. As power and/or ablation time increases, the likelihood of an impedance rise also increases. As a result of this process, there has been a natural upper bound on the amount of energy which can be delivered to cardiac tissue and therefore the size of RF lesions. Historically, RF lesions have been hemispherical in shape with maximum lesion dimensions of approximately 6 mm in diameter and 3 to 5 mm in depth.

In clinical practice, it is desirable to reduce or eliminate impedance rises and, for certain cardiac arrhythmias, to create larger lesions. One method for accomplishing this is to monitor the temperature of the ablation electrode and to control the RF current delivered to the ablation electrode based on this temperature. If the temperature rises above a preselected value, the current is reduced until the temperature drops below this value. This method has reduced the number of impedance rises during cardiac ablations but has not significantly increased lesion dimensions. The results are not significantly different because this method still relies on the cooling effect of the blood which is dependent on location in the heart and orientation of the catheter to endocardial surface.

Another method is to irrigate the ablation electrode, e.g., with physiologic saline at room temperature, to actively cool the ablation electrode instead of relying on the more passive physiological cooling of the blood. Because the strength of the RF current is no longer limited by the interface temperature, current can be increased. This results in lesions which tend to be larger and more spherical, usually measuring about 10 to 12 mm.

The clinical effectiveness of irrigating the ablation electrode is dependent upon the distribution of flow within the electrode structure and the rate of irrigation flow through the tip. Effectiveness is achieved by reducing the overall electrode temperature and eliminating hot spots in the ablation electrode which can initiate coagulum formation. More channels and higher flows are more effective in reducing overall temperature and temperature variations, i.e., hot spots. The coolant flow rate must be balanced against the amount of fluid that can be injected into a patient and the increased clinical load required to monitor and possibly refill the injection devices during a procedure. In addition to irrigation flow during ablation, a maintenance flow, typically at a lower flow rate, is required throughout the procedure to prevent backflow of blood flow into the coolant passages. Thus reducing coolant flow by utilizing it as efficiently as possible is a desirable design objective.

One method for designing an ablation electrode which efficiently utilizes coolant flow is the use of a porous material structure. Such a design is described, for example, in U.S. Pat. Nos. 5,643,197 and 5,462,521 to Brucker et al. The use of a porous material in which tiny particles are sintered together to form a metallic structure provides a multiplicity of interconnected passages which allow for efficient cooling of an electrode structure. Additionally, the porous structure provides a uniform flow distribution of perfusate over the outside surface of the electrode which acts as a barrier layer between the blood and the electrode surface. This barrier layer prevents contact with the blood and the electrode further minimizing the possibility of coagulum formation on the catheter tip. This effect is important in regions where flow may be reduced by other structures such as temperature sensors and attachment methods.

Previously attempts have been made to design an irrigated tip catheter having a porous tip electrode made of a sintered material through which saline or other fluid can pass. However, Brucker et al. do not describe how various components, such as a thermocouple, lead wire or fluid tube, are mounted into the porous electrode. If these components are mounted in the traditional manner, i.e., by gluing or soldering them directly to the electrode, the glue or solder tends to seep into and through the porous material, thus reducing or even completely blocking the flow of cooling fluid through the porous material. Accordingly, a need exists for a porous tip electrode design in which various components can be mounted without blocking the flow of fluid through the porous material. In addition, the design of an irrigated tip electrode requires extensive testing at the bench and animal levels to verify that it provides the desired safety and clinical benefits, Accordingly, a need exists for a tip electrode design that reduces the complexity inherent during development of current cooled electrode designs.

SUMMARY OF THE INVENTION

In one embodiment, the present invention is directed to a porous tip electrode for a catheter. The electrode comprises a body and an insert. The body comprises a porous material through which fluid can pass and has a cavity therein. The insert comprises a non-porous material, is contained within the cavity, and has at least one passage extending therethrough. By providing separate structures for the mechanical and hydraulic functions, changes in catheter design, e.g., changes in diameter or number of lumens, the insert can be redesigned without altering the design of the porous body. This has the distinct advantage of requiring less testing to ensure the electrode provides its desired clinical benefit.

In a particlarly preferred embodiment, the body is in the form of a shell having a radius, a cylindrical sidewall, an open interior and a hemispherical cap at its distal end. Preferably the cylindrical sidewall of the shell has a uniform thickness. The porous shell is designed to achieve efficient cooling of the electrode structure and to maintain a uniform layer of perfusate around the outside surface of the electrode.

In another embodiment, the invention is directed to an irrigated tip catheter having a porous tip electrode. The catheter comprises a catheter body and a tip section. The catheter body has an outer wall, proximal and distal ends, and a lumen extending therethrough. The tip section comprises a segment of flexible tubing having proximal and distal ends and at least one lumen therethrough. The proximal end of the tip section is fixedly attached to the distal end of the catheter body. The porous tip electrode is fixedly attached to the distal end of the tubing of the tip section. The tip electrode has an outer surface and comprises a body and an insert. The body comprises a porous material through which fluid can pass and has a cavity therein. The insert, which comprises a non-porous material, is contained within the cavity of the body. The insert has at least one passage extending therethrough in fluid communication with a lumen in the tip section. An infusion tube having proximal and distal ends extends through the central lumen in the catheter body. The distal end of the infusion tube is in fluid communication with the proximal end of the passage in the tip electrode, whereby fluid can flow through the infusion tube, into the passage in the tip electrode and through the porous material of tip electrode to the outer surface of the tip electrode.

DESCRIPTION OF THE DRAWINGS

These and other features and advantages of the present invention will be better understood by reference to the following detailed description when considered in conjunction with the accompanying drawings wherein:

FIG. 3A is a side cross-sectional view of a catheter tip section showing the lumens for the fluid passage and puller wire.

DETAILED DESCRIPTION

In a particularly preferred embodiment of the invention, there is provided a steerable catheter having an irrigated tip. As shown in FIGS. 1 to 4, catheter 10 comprises an elongated catheter body 12 having proximal and distal ends, a tip section 14 at the distal end of the catheter body 12, and a control handle 16 at the proximal end of the catheter body 12.

Figure 1:
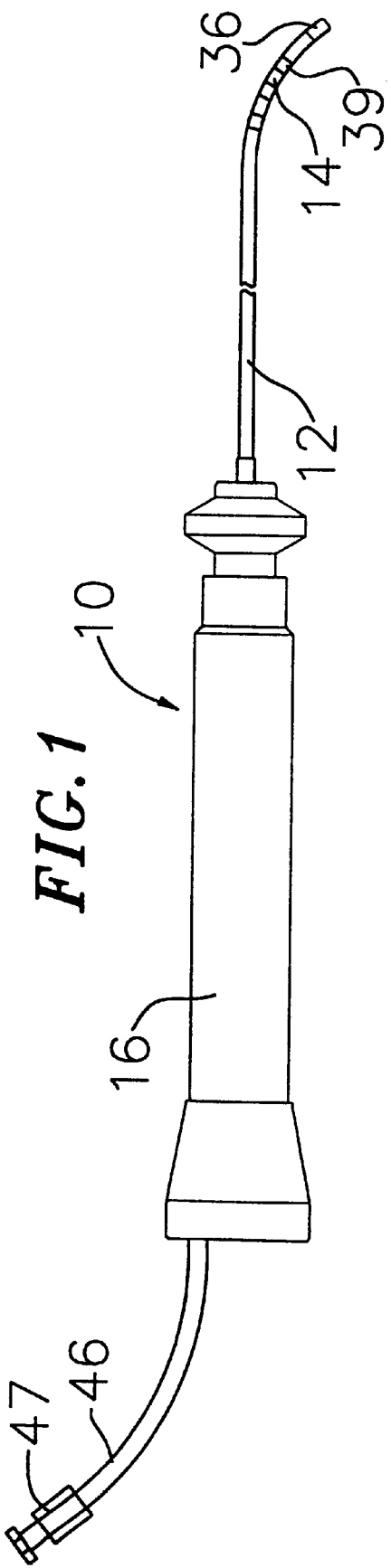
FIG. 1 is a side view of an embodiment of the catheter of the invention.
Figure 2:
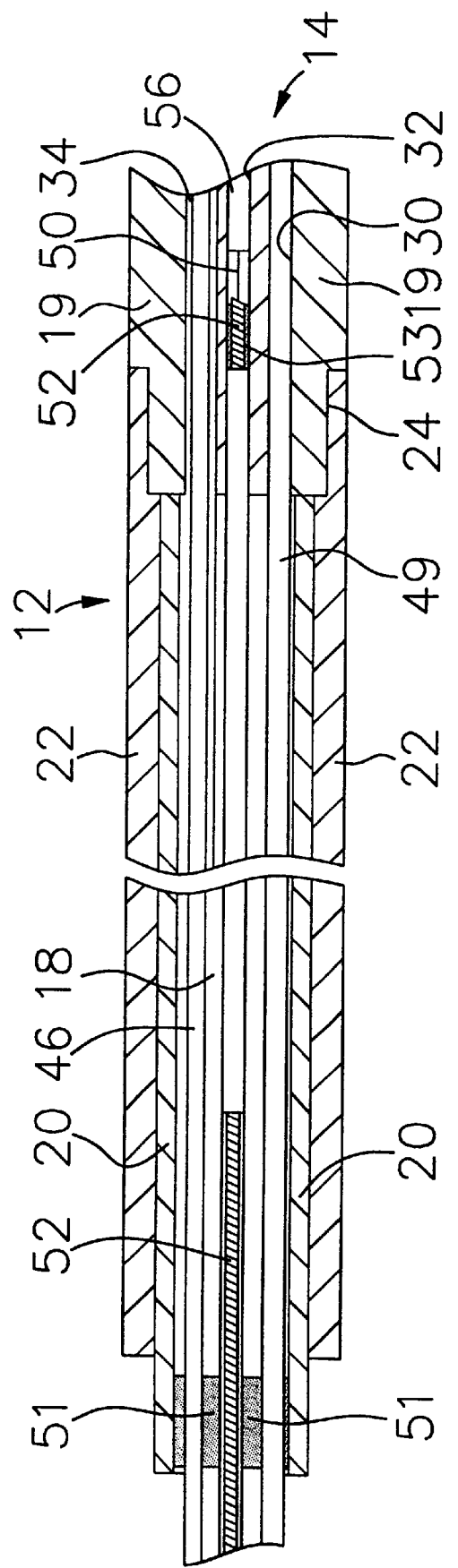
FIG. 2 is a side cross-sectional view of a catheter body according to the invention, including the junction between the catheter body and tip section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane, or PEBAX. The outer wall 22 comprises an imbedded braided mesh of high-strength steel, stainless steel or the like to increase torsional stiffness of the catheter body 12 so that, when the control handle 16 is rotated, the tip section 14 of the catheter 10 will rotate in a corresponding manner. The outer diameter of the catheter body 12 is not critical, but is preferably no more than about 8 french, more preferably about 7 french, still more preferably about 5 french. Likewise the thickness of the outer wall 22 is not critical, but is thin enough so that the central lumen 18 can accommodate an infusion tube, a puller wire, lead wires, and any other wires, cables or tubes. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness. A particularly preferred catheter has an outer wall 22 with an outer diameter of from about 0.090 inch to about 0.098 inch and an inner diameter of from about 0.061 inch to about 0.065 inch and a polyimide stiffening tube 20 having an outer diameter of from about 0.060 inch to about 0.064 inch and an inner diameter of from about 0.051 inch to about 0.056 inch.

Figure 3B:
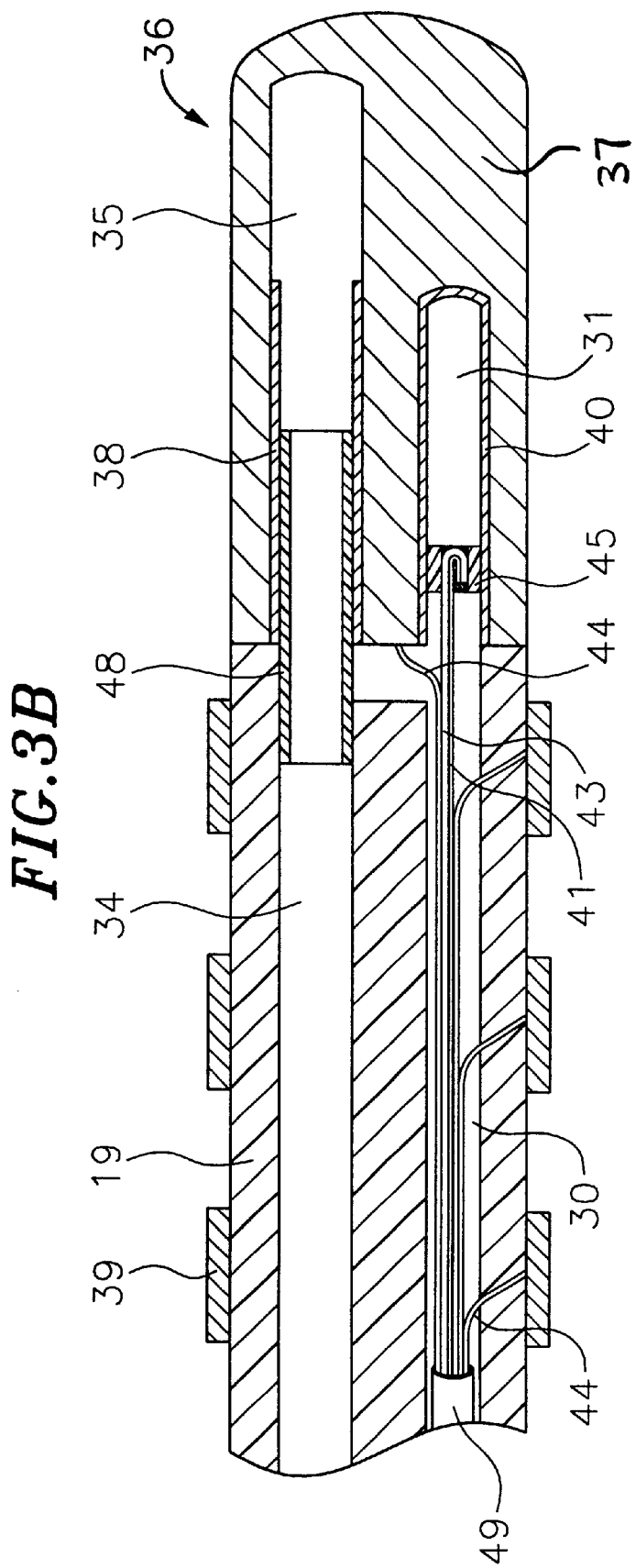
FIG. 3B is a side cross-sectional view of the catheter tip section of FIG. 3A showing the lumens for the fluid passage and thermocouple and electrode lead wires.
Figure 4:
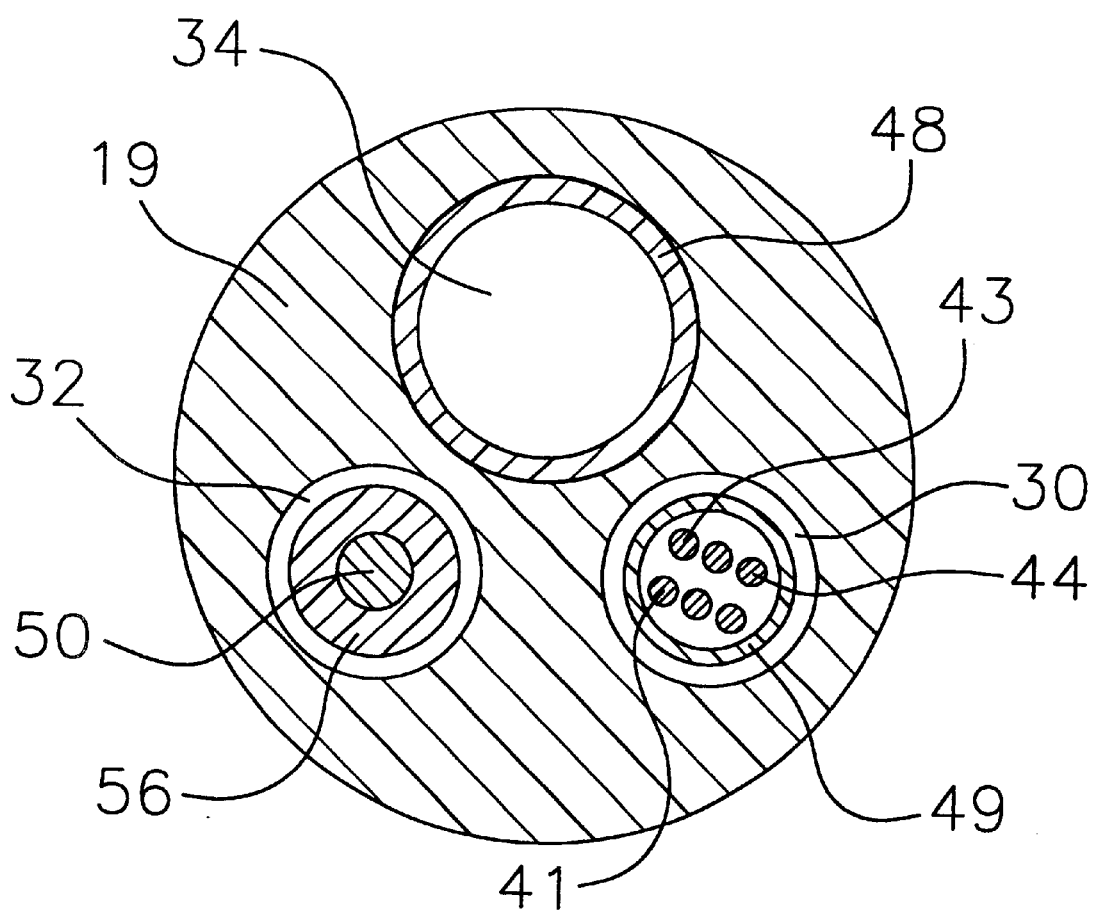
FIG. 4 is a longitudinal cross-sectional view of the tip section illustrated in FIGS. 3A and 3B.

As shown in FIGS. 3A, 3B and 4, the tip section 14 comprises a short section of tubing 19 having three lumens 30, 32 and 34. The tubing 19 is made of a suitable non-toxic material that is preferably more flexible than the catheter body 12. A presently preferred material for the tubing 19 is braided polyurethane, i.e., polyurethane with an embedded mesh of braided high-strength steel, stainless steel or the like. The outer diameter of the tip section 14, like that of the catheter body 12, is preferably no greater than about 8 french, more preferably 7 french, still more preferably about 5 french. The size of the lumens is not critical. In a particularly preferred embodiment, the tip section 14 has an outer diameter of about 7 french (0.092 inch) and the first lumen 30 and second lumen 32 are generally about the same size, each having a diameter of from about 0.020 inch to about 0.024 inch, preferably 0.022 inch, with the third lumen 34 having a slightly larger diameter of from about 0.032 inch to about 0.038 inch, preferably 0.036 inch.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by adhesive (e.g., polyurethane glue) or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint (not shown) with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter a second glue joint (not shown) is formed between the proximal ends of the stiffening tube 20 and outer wall 22 using a slower drying but stronger glue, e.g., polyurethane.

Figure 14:
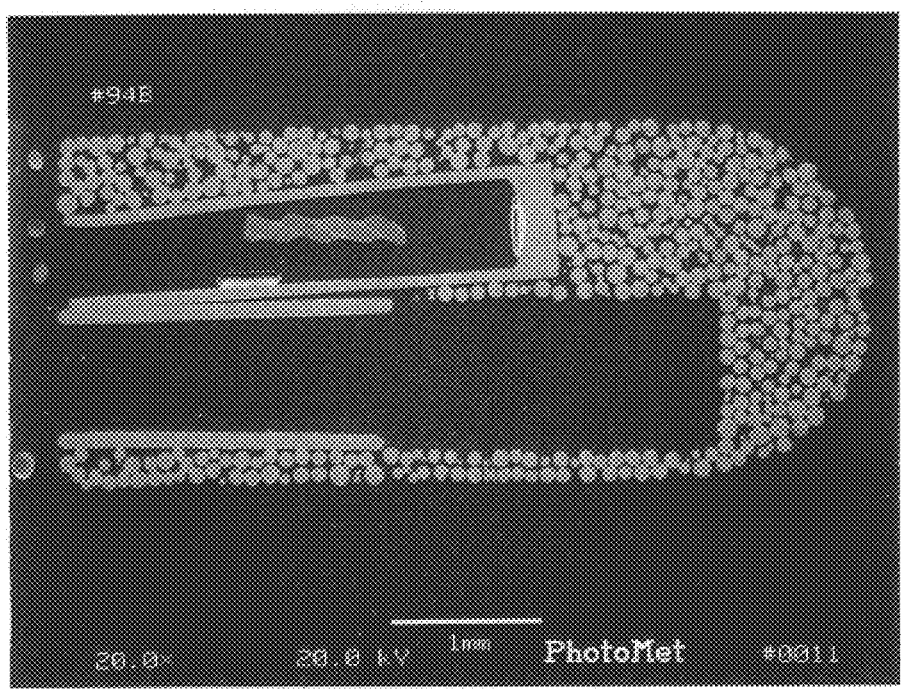
FIG. 14 is a photograph of a tip electrode according to the invention.
Figure 15:
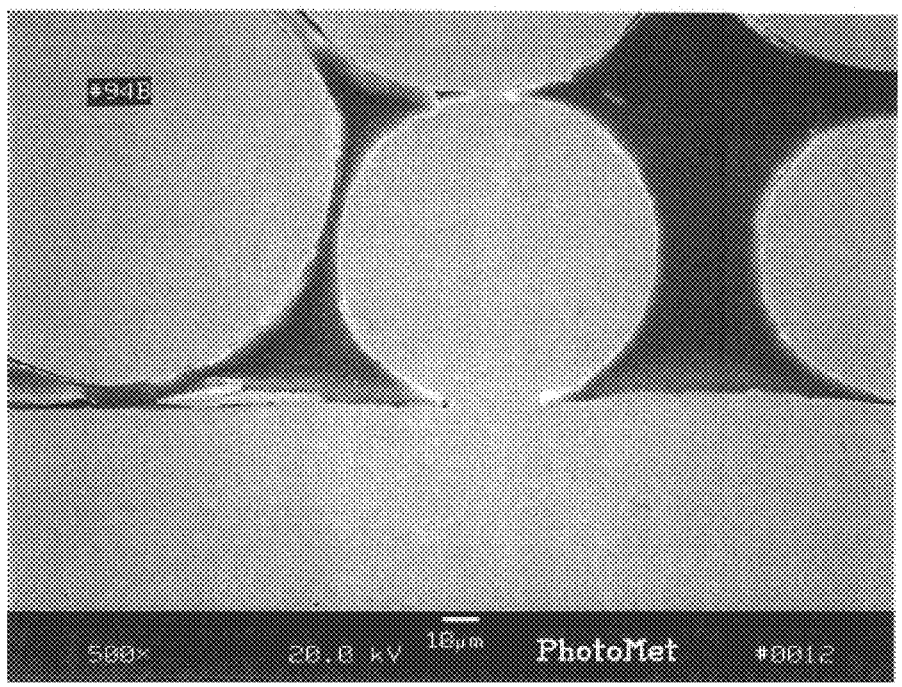
FIG. 15 is a photograph of a close-up view of the tip electrode according to FIG. 14.
Figure 16:
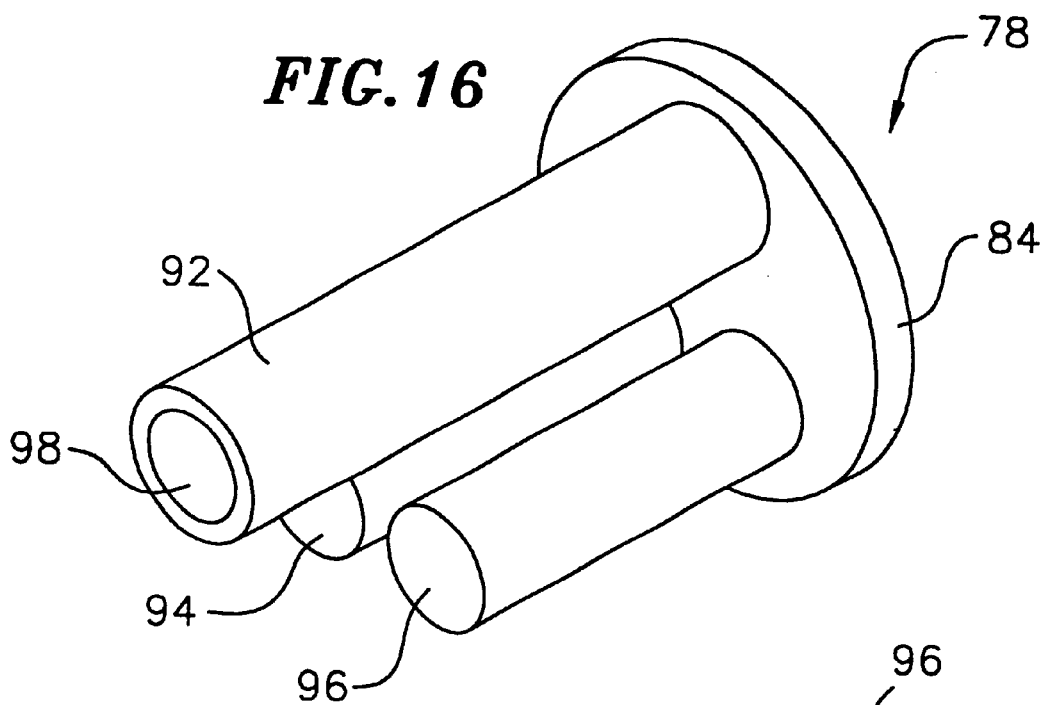
FIGS. 16 and 17 are prospective schematic views of an insert for an alternative tip electrode according to the invention.
Figure 17:
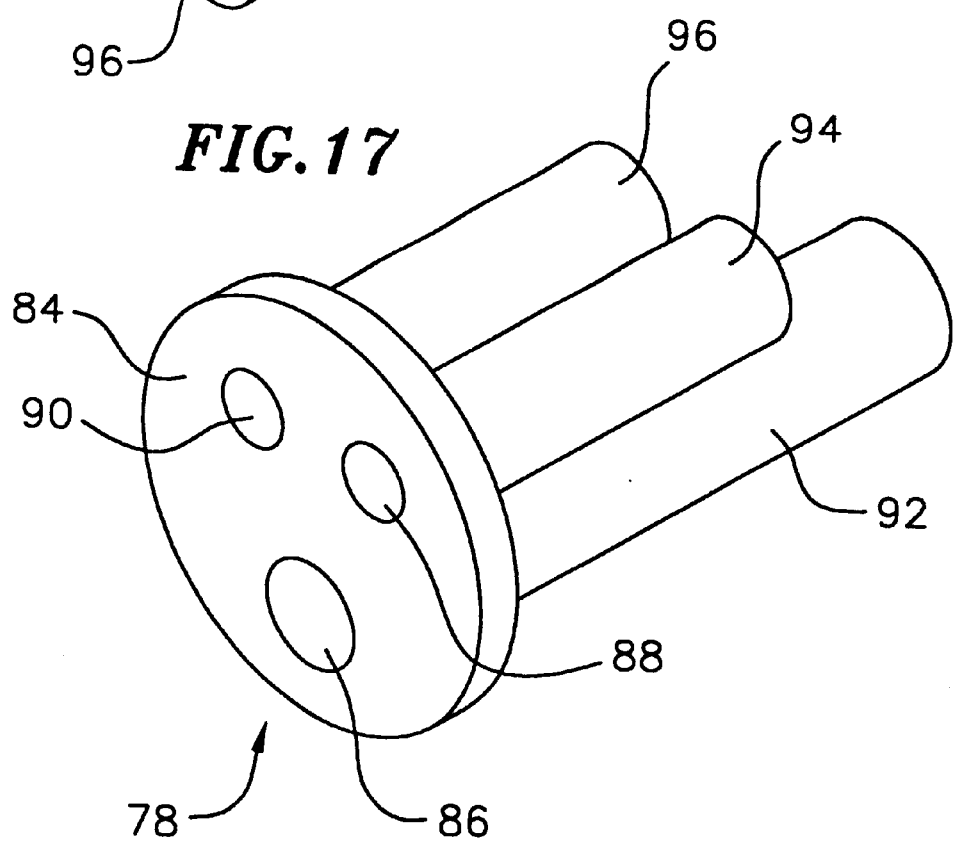
Figure 18:
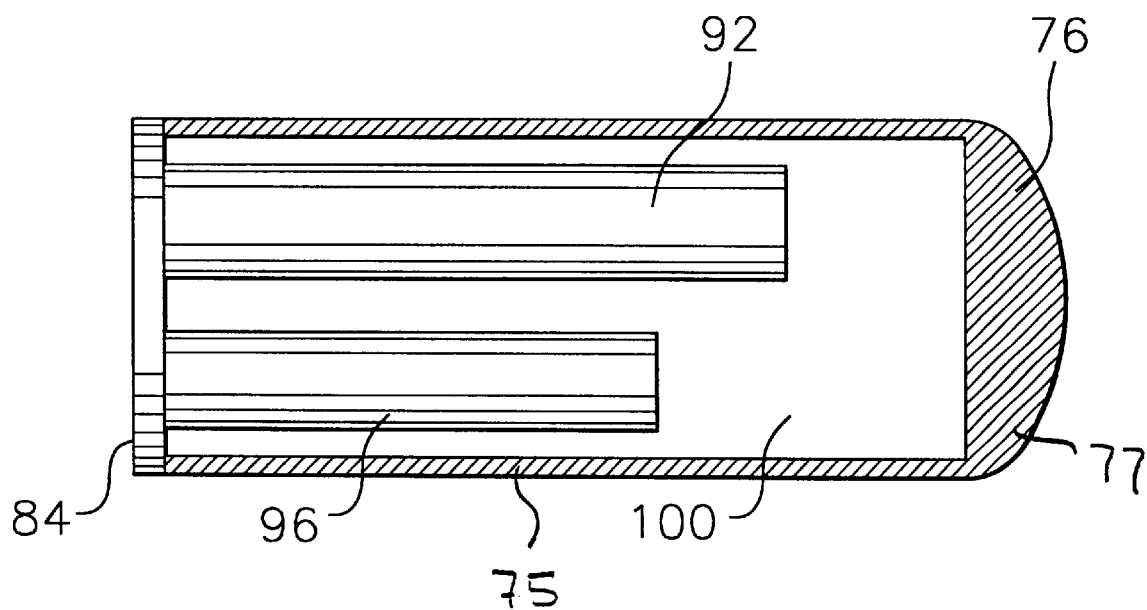
FIG. 18 is a side cross-sectional view of an electrode including the insert of FIGS. 16 and 17.

At the distal end of the tip section 14 is a tip electrode 36. Preferably the tip electrode 36 has a diameter about the same as the outer diameter of the tubing 19. The tip electrode 36 comprises a body 37 having at least one cavity and at least one insert therein, as described in more detail below. The body 37 of the tip electrode 36 is formed of any suitable porous material, for example, a tightly woven screen or a deep drawn metal cup in which holes are drilled. Preferably the porous material is sintered metal material formed from metal particles, preferably platinum-iridium (e.g., 90% platinum/10% iridium [Pt/Ir]), as best depicted in FIGS. 14 and 15. However, the sintered material can be formed from any other biocompatible metal particles, for example, stainless steel or titanium. As used herein, the term "sinter" refers to the process of bonding adjacent particles in a powder mass or compact by heating to a temperature below the melting point of the main constituent at a predetermined and closely controlled time-temperature regime including the heating and cooling phase in a protective atmosphere. A description of suitable metal materials for use in the present sintered electrode is provided in U.S. Pat. Nos. 5,643,197, 5,462,521, and 3,855,638, the disclosures of which are incorporated herein by reference. The sintered material permits passage of a cooling fluid through the tip electrode, as described in more detail below. The porosity of the sintered material is controlled by the amount of particle compacting in the mold or glue, the particle size, and the particle distribution.

A particular preferred sintering process involves providing Pt/Ir alloy powder particles in a certain sieve fraction, e.g., in the range of from about 5 microns to about 250 microns. The particles are preferably in the range of from about 10 microns to about 100 microns. In a particularly preferred embodiment, at least two different sized particles can be provided. For example, particles in the range of from about 15 microns to about 30 microns, and more preferably about 20 microns, in combination with particles in the range of from about 80 microns to about 110 microns, and more preferably about 100 microns, could be used. When two different sized particles are used, preferably the larger particles have a mean diameter at least about 2.5 times greater than the mean diameter of the smaller particles, and more preferably at least about 4 times greater. Alternatively a single particle size can be used, which can give a denser packing and result in a higher pressure drop across the porous body. Whatever alloy is used, it is the metal particles are preferably rounded, and more preferably spherical, so provide a tip electrode surface that is not rough. In another alternative embodiment, the particles can be irregular particles, i.e., having different shapes, which is a low-cost alternative.

In a preferred process, the particles are put into a mold, such as ceramic mold, having the desired electrode shape. If desired, the particles can be mixed with a suitable binder prior to being put into the mold. When a binder is used, the mold containing the binder and particles is placed into a low temperature oven and heated to a temperature sufficient to evaporate the binder. The particles are then sintered under vacuum or air at a temperature ranging from about 1200° C. to about 1600° C., although the temperature can vary depending on the alloy composition, which should be below the melting point of the composition. The resulting tip electrode is then removed from the mold and assembled onto the flexible tubing of the tip section. Other methods for manufacturing the sintered porous material are described in U.S. Pat. Nos. 3,855,638, 4,101,984 and 4,934,381, the disclosures of which are incorporated herein by reference.

A tip electrode prepared in accordance with this method is depicted in FIGS. 14 and 15. In particular, these photographs illustrate the porosity of the tip electrode when particles of different sizes are used. Although the drawings of the tip electrode, such as FIGS. 3A and 3B, do not depict the porous sintered material in detail, it is to be understood that where the body of the tip electrode is described as being made of a porous sintered material, it appears generally as depicted in FIGS. 14 and 15. The drawings, such as FIGS. 3A and 3B, are provided to more clearly show the additional components in the tip section.

As shown in FIGS. 3A and 3B, the body 37 of the tip electrode 36 has three cavities extending therein, namely a primary fluid passage 35 and first and second blind holes 31 and 33 that correspond in size and location to the three lumens 34, 30 and 32, respectively, in the tip section 14. The primary fluid passage 35 extends substantially all the way through the sintered material of the body 37 of the tip section 36, preferably ending just before the distal end of the body. The blind holes 31 and 33 extend only a part of the way through the sintered material of the body 37, preferably about half the length of the body or less. For example, for a 3.5 mm tip electrode 36, the first and second blind holes 31 and 33 are each about 0.088 inch long.

Contained within the cavities of the body 37 are three inserts, namely a hollow metal tube 38 and first and second hollow metal cups 40 and 42. The hollow metal tube 38 and first and second hollow metal cups 40 and 42 are made of a non-porous, preferably solid metal, material. Preferably the hollow metal tube 38 and hollow metal cups 40 and 42 are made of platinum-iridium (e.g., 90% platinum/10% iridium [Pt/Ir]). The hollow metal tube 38, which has a passage or bore therethrough, extends part way into the proximal end of the primary fluid passage 35. Preferably the hollow tube 38 is approximately half the length of the primary fluid passage 35. The first and second hollow metal cups 40 and 42 extend into the first blind hole 31 and second blind hole 33, respectively. The hollow cups 40 and 42 are open at their proximal ends and closed at their distal ends.

By this design, various tubes and wires, discussed in more detail below, mounted in the tip electrode 36 are bonded directly to the hollow tube 38 and hollow cups 40 and 42, e.g., by solder, glue or the like, and not to the sintered material of the body 37. The solder, glue, or the like does not spread into the sintered material of the body 37, and therefore do not block the pores and prevent maximum flow of cooling fluid through the body.

Preferably, the hollow metal tube and metal cups are formed into the body 37 during the sintering process. Specifically, before the metal particles are sintered together (but after the binder has been evaporated), the hollow tube and cups are put into place adjacent the metal particles. Preferably, the mold is formed to hold the tube and cups in place. The metal particles are then sintered to each other and to the hollow tube and cups. This method avoids the need for the additional manufacturing step of welding the hollow tube and cups to the body 37.

A preferred tip electrode has a length ranging from about 2.5 mm to about 8 mm, preferably about 3.5 mm. Preferably the tip electrode 36 is attached to the tubing 19 by polyurethane glue or the like. The wires and tubes that extend into the tip electrode 36, described in more detail below, help to keep the tip electrode in place on the tubing 19 of the tip section 14.

In the embodiment shown, there are three ring electrodes 39 mounted on the tubing 19 proximal to the tip electrode 36. It is understood that the presence and number of ring electrodes 39 may vary as desired. Each ring electrode 39 is slid over the tubing 19 and fixed in place by glue or the like. The ring electrodes 39 can be made of any suitable material, and are preferably machined from platinum-iridium bar (90% platinum/10% iridium).

The tip electrode 36 and ring electrodes 39 are each connected to a separate lead wire 44. The lead wires 44 extend through the first lumen 30 of tip section 14, the central lumen 18 of the catheter body 12, and the control handle 16, and terminate at their proximal end in an input jack (not shown) that may be plugged into an appropriate monitor (not shown). The portion of the lead wires 44 extending through the central lumen 18 of the catheter body 12, control handle 16 and proximal end of the tip section 14 may be enclosed within a protective sheath 49, which can be made of any suitable material, preferably polyimide. The protective sheath 49 is preferably anchored at its distal end to the proximal end of the tip section 14 by gluing it in the first lumen 30 with polyurethane glue or the like.

The lead wires 44 are attached to the tip electrode 36 and ring electrodes 39 by any conventional technique. Connection of a lead wire 44 to the tip electrode 36 is accomplished, for example, by soldering the lead wire 44 into the second hollow cup 42 in the second hole 33 of the tip electrode, as shown in FIG. 3A.

Connection of a lead wire 44 to a ring electrode 39 is preferably accomplished by first making a small hole through the tubing 19. Such a hole can be created, for example, by inserting a needle through the tubing 19 and heating the needle sufficiently to form a permanent hole. A lead wire 44 is then drawn through the hole by using a microhook or the like. The ends of the lead wire 44 are then stripped of any coating and soldered or welded to the underside of the ring electrode 39, which is then slid into position over the hole and fixed in place with polyurethane glue or the like.

A fluid tube is provided within the catheter body 12 for infusing fluids, e.g., saline, to cool the tip electrode 36. The fluid tube may be made of any suitable material, and is preferably made of polyimide tubing. A preferred fluid tube has an outer diameter of from about 0.032 inch to about 0.036 inch and an inner diameter of from about 0.027 inch to about 0.032 inch.

With reference to FIGS. 2 and 3A, the fluid tube comprises multiple tube segments. A first fluid tube segment 46 extends through the central lumen 18 of the catheter body 12 and terminates in the proximal end of the third lumen 34 of the tip section 14. The distal end of the first fluid tube segment 46 is anchored in the third lumen 34 by polyurethane glue or the like. The proximal end of the first fluid tube segment 46 extends through the control handle 16 and terminates in a luer hub 47 or the like at a location proximal to the control handle. A second fluid tube segment 48 is provided at the distal end of the third lumen 34 and extends into the primary fluid passage 35 of the tip electrode 36. The second fluid tube segment 48 is anchored by polyurethane glue or the like within the third lumen 34 of the tip section 14 and in the hollow tube 38 in the primary fluid passage 35. The second fluid tube segment 48 provides additional support to maintain the tip electrode 36 mounted on the tubing 19. In practice, fluid is injected into the first fluid tube segment 46 through the luer hub 47 and flows through the first fluid tube segment 46, through the third lumen 34, through the second fluid tube segment 48, into the hollow tube 38 in the primary fluid passage 35 of the tip electrode 36, and out through the porous, sintered material of the tip electrode. Because the primary fluid passage 35 extends distally a greater length than the first and second blind holes 31 and 33, the fluid can pass outwardly on all sides of the distal end of the primary fluid passage.

The fluid introduced through the catheter is preferably a biologically compatible fluid, and may be in a gaseous or liquid state. Suitable fluids include saline, water, carbon dioxide, nitrogen, and helium. In addition to, or instead of, being used to cool the tip electrode, the infused fluid also forms a buffer layer to maintain biological materials, such as blood, at a distance from the tip electrode, thereby minimizing contact of the tip electrode with the biological material. This buffer layer reduces coagulation of biological materials and regulates the impedance or resistance to energy transfer of the tissue near the tip electrode during ablation.

The rate of fluid flow through the catheter may be controlled by any suitable fluid infusion pump or by pressure. A suitable infusion pump is the FLOGARD™ available from Baxter. The rate of fluid flow through the catheter preferably ranges from about 0.5 ml/min to about 30 ml/min, more preferably from about 5 ml/min to about 15 ml/min. Preferably the fluid is maintained at about room temperature.

A temperature sensing means is provided for the tip electrode 36 and, if desired, the ring electrodes 39. Any conventional temperature sensing means, e.g., a thermocouple or thermistor, may be used. With reference to FIG. 3B, a preferred temperature sensing means for the tip electrode 36 comprises a thermocouple formed by a wire pair. One wire of the wire pair is a copper wire 41, e.g., a number 40 copper wire. The other wire of the wire pair is a constantan wire 43, which gives support and strength to the wire pair. The wires 41 and 43 of the wire pair are electrically isolated from each other except at their distal ends where they contact and are twisted together, covered with a short piece of plastic tubing 45, e.g., polyimide, and covered with epoxy. The plastic tubing 45 is then attached by polyurethane glue or the like in first hollow cup 40 in the first blind hole 31 of the tip electrode 36. The wires 41 and 43 extend through the first lumen 30 in the tip section 14. Within the catheter body 12, the wires 41 and 43 may extend through the protective sheath 49 with the lead wires 44. The wires 41 and 43 then extend out through the control handle 16 and to a connector (not shown) connectable to a temperature monitor (not shown).

Alternatively, the temperature sensing means may be a thermistor. A suitable thermistor for use in the present invention is Model No. AB6N2-GC14KA143E/37C sold by Thermometrics (New Jersey). The temperature sensing means may also be used as a feedback system to adjust the flow rate of the fluid through the catheter to maintain a desired temperature at the tip electrode.

A puller wire 50 extends through the catheter body 12, is anchored at its proximal end to the control handle 16, and is anchored at its distal end to the tip section 14. The puller wire 50 is made of any suitable metal, such as stainless steel or Nitinol, and is preferably coated with Teflon® or the like. The coating imparts lubricity to the puller wire 50. The puller wire 50 preferably has a diameter ranging from about 0.006 to about 0.010 inches.

A compression coil 52 is situated within the catheter body 12 in surrounding relation to the puller wire 50. The compression coil 52 extends from the proximal end of the catheter body 12 to the proximal end of the tip section 14. The compression coil 52 is made of any suitable metal, preferably stainless steel. The compression coil 52 is tightly wound on itself to provide flexibility, i.e., bending, but to resist compression. The inner diameter of the compression coil 52 is preferably slightly larger than the diameter of the puller wire 50. The Teflon® coating on the puller wire 50 allows it to slide freely within the compression coil 52. If desired, particularly if the lead wires 44 are not enclosed by a protective sheath 49, the outer surface of the compression coil 52 can be covered by a flexible, non-conductive sheath, e.g., made of polyimide tubing, to prevent contact between the compression coil 52 and any other wires within the catheter body 12.

The compression coil 52 is anchored at its proximal end to the proximal end of the stiffening tube 20 in the catheter body 12 by glue joint 51 and at its distal end to the tip section 14 by glue joint 53. Both glue joints 51 and 53 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 52 and wicks around the outer circumference to form a glue joint about the entire circumference of the compression coil 52.

The puller wire 50 extends into the second lumen 32 of the tip section 14. The puller wire 50 is anchored at its distal end to the tip electrode 36 within the second hollow cup 42 in the second blind hole 33. A preferred method for anchoring the puller wire 50 within the tip electrode 36 is by crimping metal tubing 54 to the distal end of the puller wire 50 and soldering the metal tubing 54 inside the second hollow cup 42. Anchoring the puller wire 50 within the tip electrode 36 provides additional support for the tip electrode on the flexible plastic tubing 19, reducing the likelihood that the tip electrode will separate from the tubing. Alternatively, the puller wire 50 can be attached to the side of the tip section 14. Such a design is described in U.S. patent application Ser. No. 08/924,611 (filed Sep. 5, 1997), the disclosure of which is incorporated herein by reference. Within the second lumen 32 of the tip section 14, the puller wire 50 extends through a plastic, preferably Teflon®, sheath 56, which prevents the puller wire 50 from cutting into the wall of the tubing 19 when the tip section is deflected.

Figure 5:
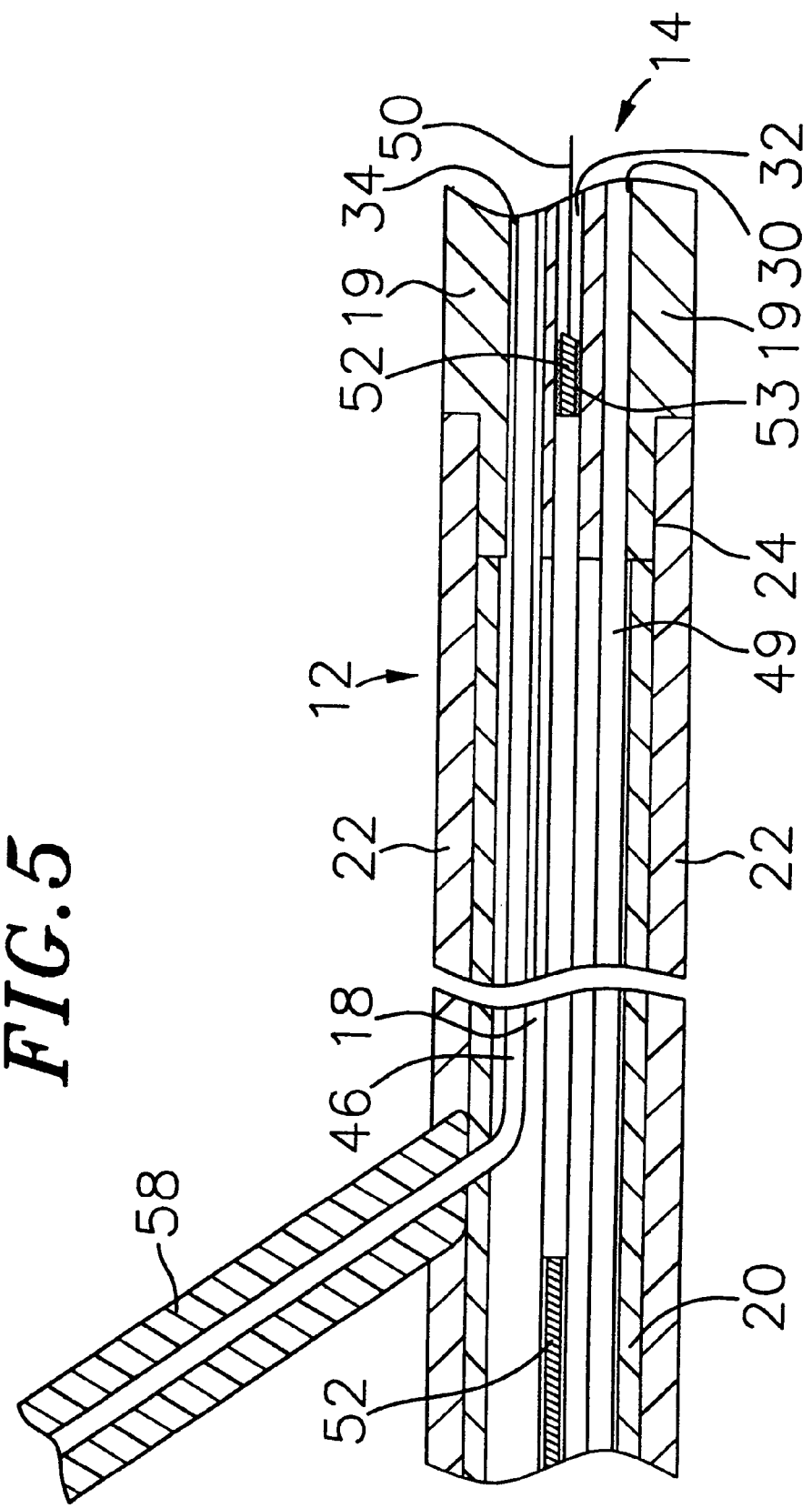
FIG. 5 is a side cross-sectional view of an alternative embodiment of a catheter body according to the invention having a side arm for an infusion tube.

In an alternative arrangement, as shown in FIG. 5, a single lumen side arm 58 is fluidly connected to the central lumen 18 near the proximal end of the catheter body 12. The first fluid tube segment 46 extends through the catheter body 12 and out the side arm 58, where it terminates in a luer hub (not shown) or the like. The side arm 58 is preferably made of the same material as the outer wall 22, but preferably has a greater thickness, e.g., 0.0275 inch. Where the side arm 58 meets the catheter body 12, a molded joint can be provided to provide additional strength and support. The molded joint can be made of any suitable biocompatable material, and is preferably made of polyurethane.

Longitudinal movement of the puller wire 50 relative to the catheter body 12, which results in deflection of the tip section 14, is accomplished by suitable manipulation of the control handle 16. A suitable control handle design for use with the present invention is described in U.S. patent application Ser. No. 08/982,113, filed Dec. 1, 1997, the disclosure of which is incorporated herein by reference.

Figure 6A:
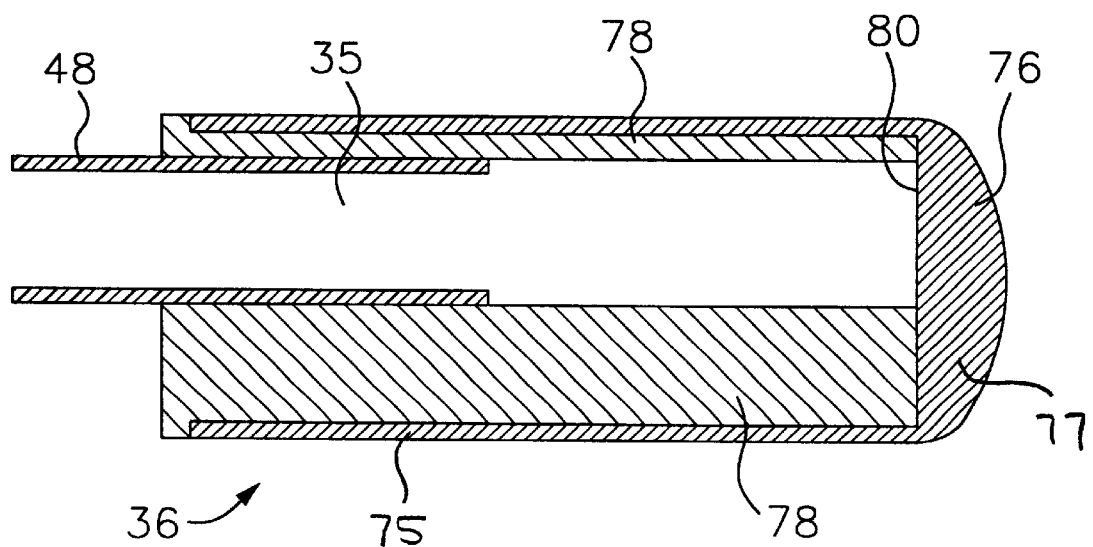
FIG. 6A is a side cross-sectional view of an alternative embodiment of a tip electrode according to the invention showing the fluid passage.
Figure 6B:
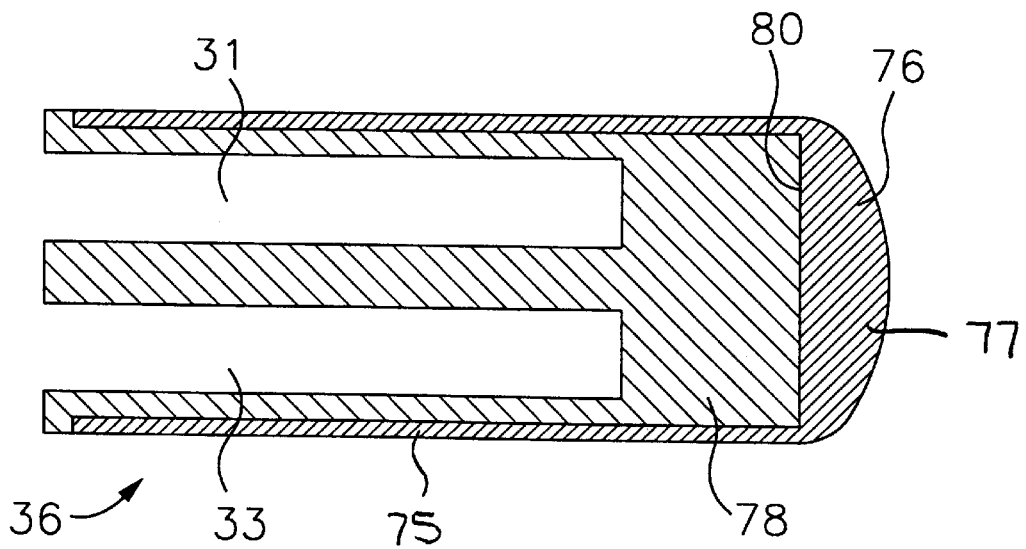
FIG. 6B is a side cross-sectional view of the tip electrode of FIG. 6A showing the blind holes for the puller wire and thermocouple and electrode lead wires.
Figure 7:
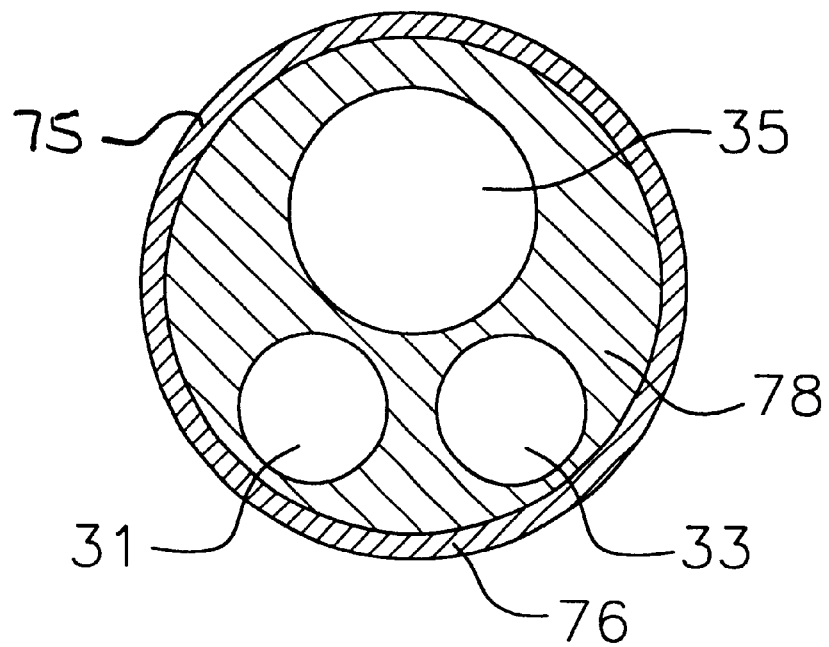
FIG. 7 is a longitudinal cross-sectional view of the tip electrode illustrated in FIGS. 6A and 6B.

An alternative embodiment of the tip electrode is depicted in FIGS. 6A, 6B and 7. The tip electrode 36 comprises a body 76 and an insert 78. The body 76 forms the distal end and the outside of the tip electrode 36 and is formed of a porous sintered metal material as described above. In this embodiment, the body 76 forms a shell having a cylindrical sidewall 75 and a hemispherical cap 77 at its distal end, wherein the cylindrical sidewall has a uniform thickness. Preferably the cylindrical sidewall 75 has a thickness equal to less than about 50% of the radius of the body 76, more preferably less than about 30% of the radius of the body. The porous shell is thus designed to achieve efficient cooling of the electrode structure and to maintain a uniform layer of perfusate around the outside surface of the electrode. In a particularly preferred embodiment, the hemispherical cap 77 has a uniform thickness that is approximately equal to the thickness of the cylindrical sidewall 75, as shown, for example, in FIG. 19.

The body 76 has a cavity 80 at its proximal end into which the insert 78 fits. Preferably the insert 78 is generally cylindrical, having a distal end surface, a proximal end surface and a cylindrical side surface. However, other shapes can be provided, for example, as shown in FIGS. 10 to 13 and described in more detail below. The insert 78 is formed of a non-porous, and preferably solid metal, material, more preferably platinum-iridium. However, any other solid suitable biocompatible metal material could also be used for the insert 78. The insert 78 has three passages that extend generally parallel to the longitudinal axis of the insert, namely a fluid passage 35, which is in contact with the body 76, and two blind holes 31 and 33, which are not in contact with the body. The second fluid tube segment 48, electrode lead wire (not shown), thermocouple wires (not shown) and puller wire (not shown) are mounted in the fluid passage 35 and blind holes 31 and 33 in a manner similar to the embodiment discussed above. The primary fluid passage 35 comprises a passage or bore that extends the full length of the solid metal insert 78, so that the distal end of the primary fluid passage is in communication with the sintered material of the body 76. The first blind hole 31 and second blind hole 33 extend into the proximal end of the insert 78 only a portion of the length of the insert, as best shown in FIG. 6B. For example, for a 3.5 mm tip electrode, the first and second blind holes 31 and 33 are each about 0.088 inch long. The second fluid tube segment 48 extends from a lumen in the tip section into the proximal end of the fluid passage 35, similar to in the embodiment of FIGS. 3A and 3B. The second fluid tube segment 48 is anchored in the fluid passage 35 by polyurethane glue or the like. The second fluid tube segment 48 extends only a part of the distance into the fluid passage 35. Fluid passes through the second fluid tube segment 48 and primary fluid passage 35, through the sintered material of the body 76, and to the exterior of the tip electrode 36.

The insert 78 and body 76 can be formed together by any process known to those skilled in the art. Preferably the insert is formed into the body of the tip electrode during the sintering process in a manner similar to the hollow tube and cups described above. Alternatively, although less desired, the insert 78 can be welded to the body 76.

Figure 8:
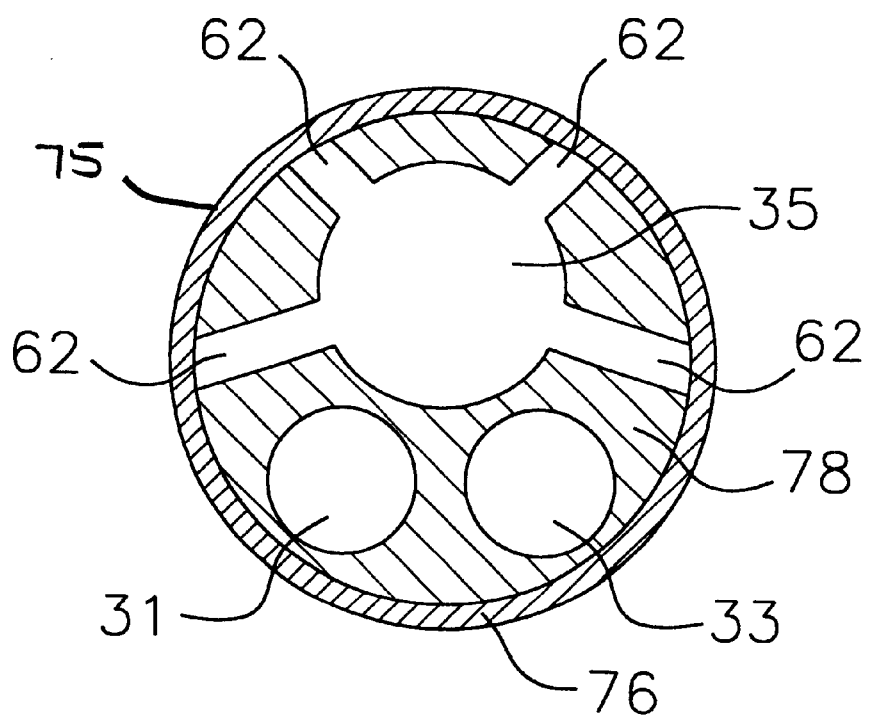
FIG. 8 is a longitudinal cross-sectional view of an alternative tip electrode according to the invention showing a branched fluid passage.

In another alternative embodiment, the tip electrode 36 comprises a body 76 and an insert 78 as shown in FIGS. 6A and 6B. However, the tip electrode 36 further comprises four transverse fluid branches 62 that extend outwardly from the primary fluid passage 35, as shown in FIG. 8. It is understood that the number and pattern of the transverse fluid branches 62 can vary as desired. The fluid branches 62 extend through the solid material of the insert 78 and come into contact with the sintered material of the body 76. Alternatively, the fluid branches 62 can extend part of the way into the sintered material of the body 76. The second fluid tube segment 48 extends from a lumen in the tip section into the proximal end of the fluid passage 35, as described above. Fluid passes from a lumen in the tip section into the second fluid tube segment 48 and fluid passage 35, through the transverse fluid branches 62 and out through the porous, sintered material of the body 76. The cooling fluid can also pass out through the porous sintered material at the distal end of body 76.

For the embodiments of FIGS. 6A, 6B, 7 and 8, in a manner similar to the embodiment of FIGS. 3A and 3B, thermocouple wires are mounted in the first blind hole 31 and held in place by polyurethane glue or the like. Similarly, a puller wire is anchored in the second blind hole 33 with solder or the like. An electrode lead wire is also mounted in the second blind hole 33 with the puller wire. However, in contrast to the previous embodiment, in this embodiment the solid metal insert 78 replaces the need for the hollow metal tube 38 and hollow cups 40 and 42. The solid metal material insert 78 keeps the solder and glue from blocking the porous sintered material of the body 76.

Figure 9:
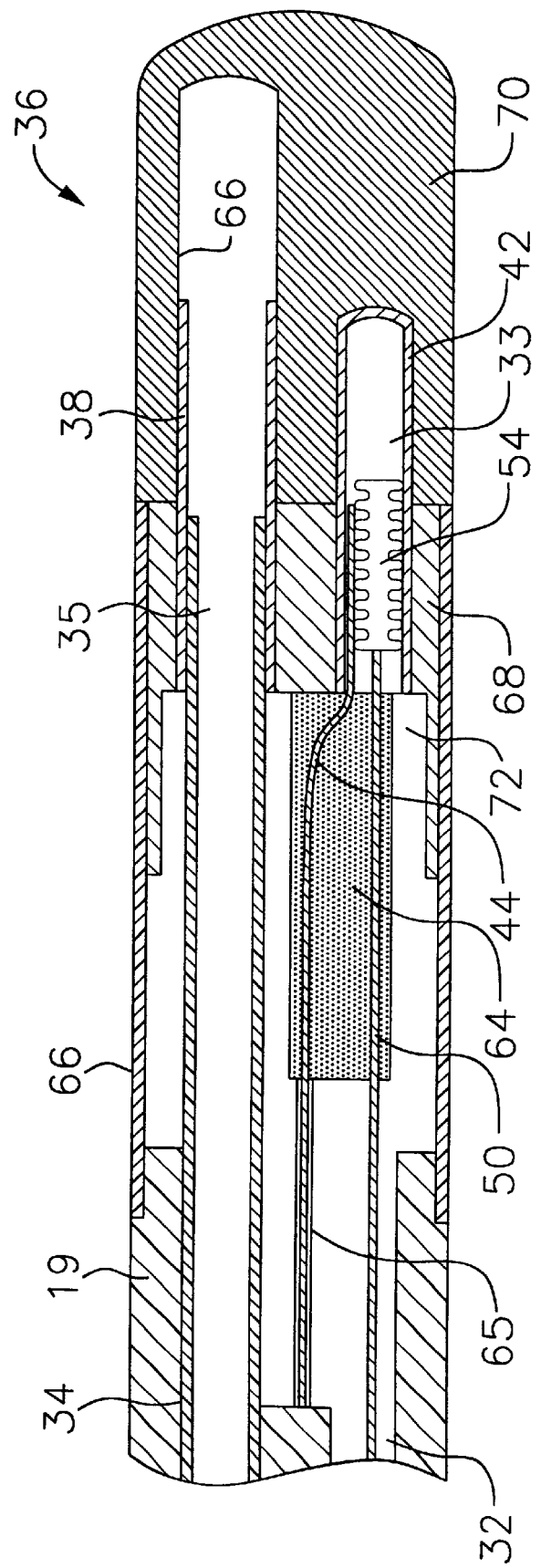
FIG. 9 is a side cross-sectional view of an alternative tip section according to the invention that houses an electromagnetic sensor.
Figure 10:
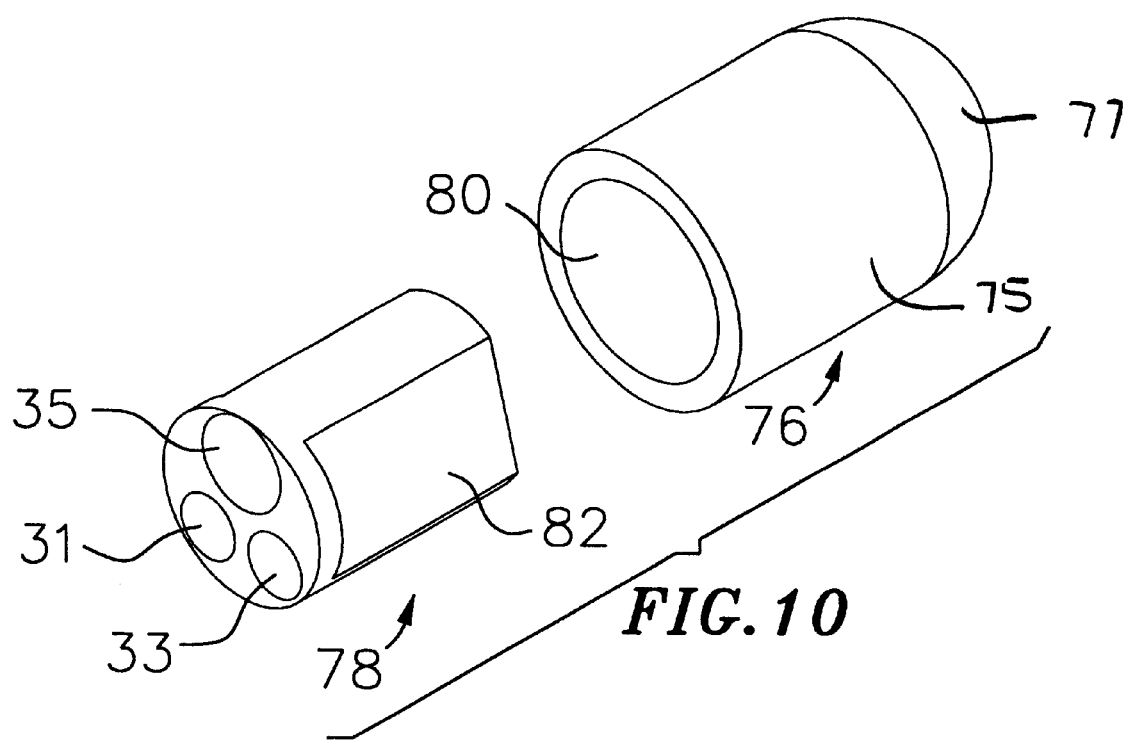
FIGS. 10 to 13 are prospective schematic views of a alternative tip electrode according to the invention.
Figure 11:
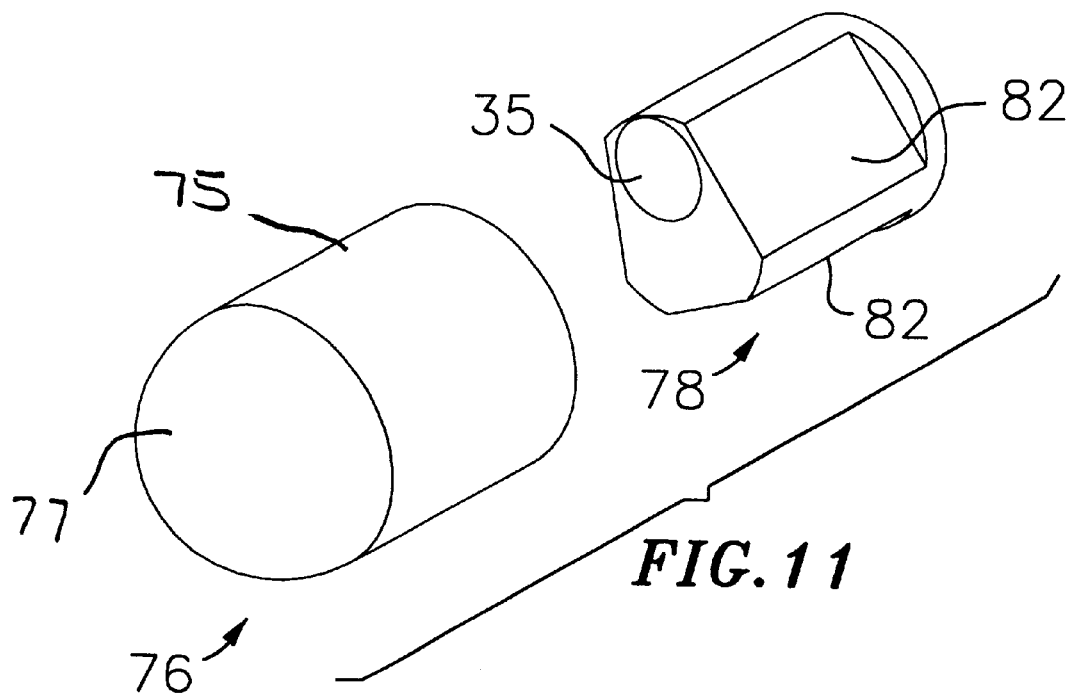
Figure 12:
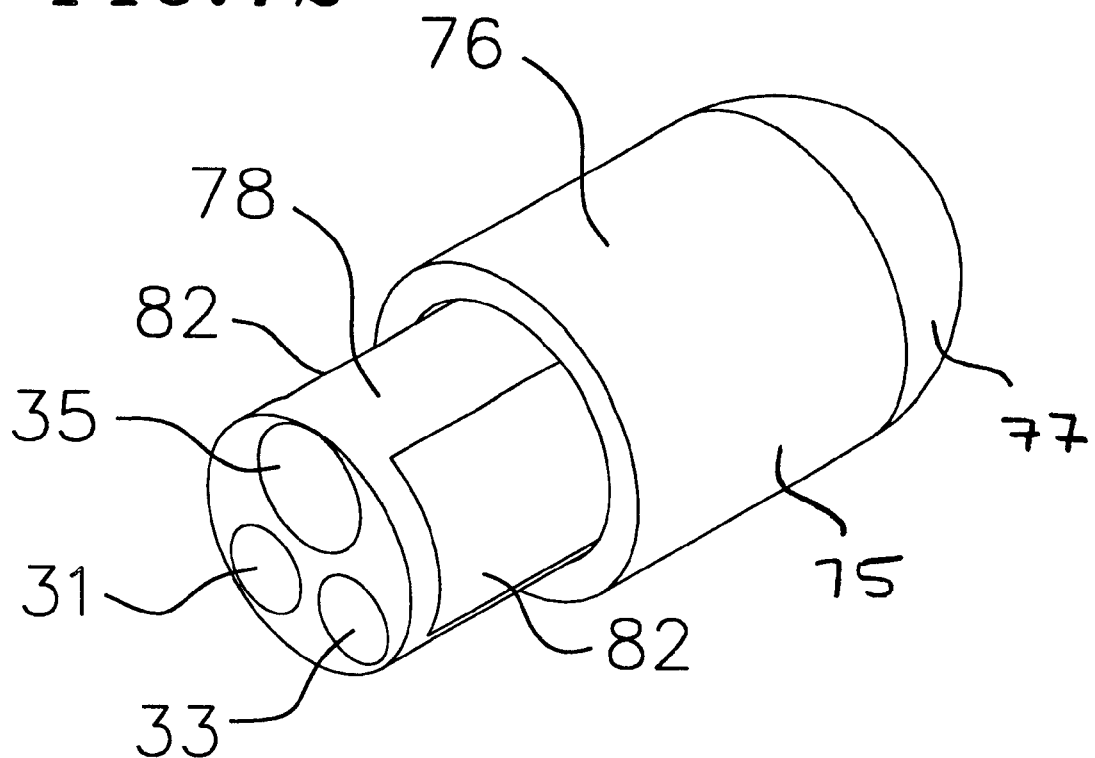
Figure 13:
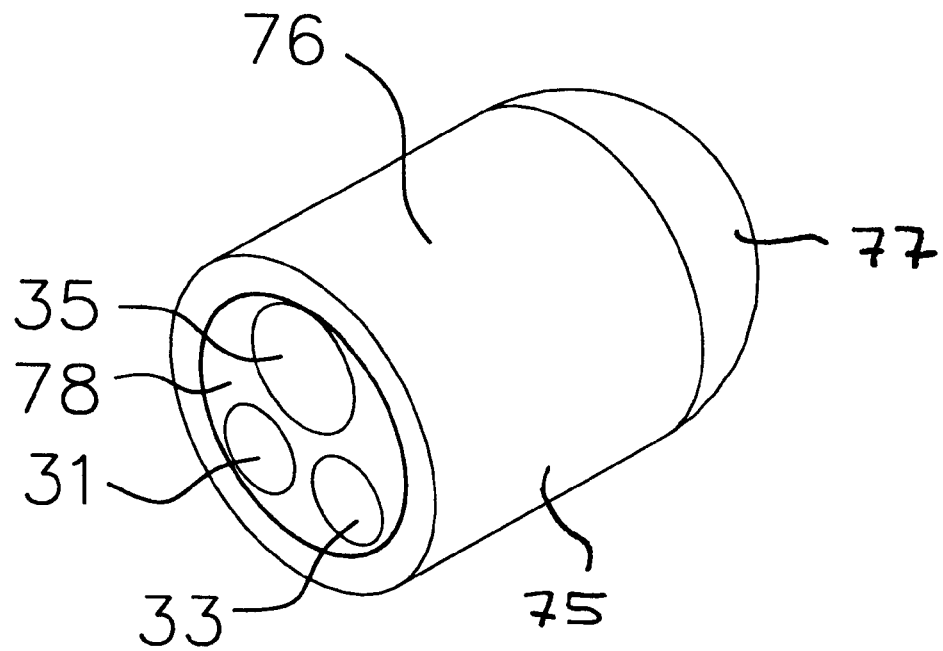

In another preferred embodiment according to the invention, an electromagnetic sensor 64 is provided in the distal end of the tip section 14. As shown in FIG. 9, in this embodiment the tip electrode 36 is connected to the tubing 19 of the tip section 14 by means of a plastic housing 66, preferably made of polyetheretherketone (PEEK). The tip electrode 36 has a proximal section 68 and a distal section 70. The proximal section 68 of the tip electrode 36 has an outer diameter less than the outer diameter of the distal section 70. Thus, in the depicted embodiment, the proximal section 68 forms a recessed stem that fits inside the distal end of the plastic housing 66, and the distal section 70 is exposed. The proximal section 68 is bonded to the housing 66 by polyurethane glue or the like. The proximal end of the plastic housing 66 is bonded with polyurethane glue or the like to the distal end of the tubing 19 of the tip section 14. Preferably the plastic housing 66 is about 1 cm long.

In this embodiment, the tip electrode 36 preferably has a total length ranging from about 6 mm to about 9 mm, more preferably about 7 mm. For a 7 mm long tip electrode, the distal section and proximal section 68 each preferably have a length of about 3.5 mm. The proximal section 68 is formed of a solid metal material, similar to the solid metal material described in the previous embodiment. The distal section 70 is formed of a porous sintered material 29, also as described above. However, the tip electrode could be modified so that a portion of the proximal section 68, which is formed of a solid material, is exposed along with the distal section 70, which is formed of the porous material 29. Alternatively, a portion of the distal section 70 could form a part of the stem that extends into the housing 66. However, in the preferred embodiment, the entire porous distal section 70 is exposed and the entire solid proximal section 68 is contained within the housing 66.

A generally hollow cavity 72 is formed in the proximal end of the proximal section 68 of the tip electrode 36. The electromagnetic sensor 64 is mounted partially in the plastic housing 66, partially in the cavity 72, and partially in the flexible tubing 19, in a manner similar to that described in U.S. patent application Ser. No. 08/982,113, the disclosure of which is incorporated herein by reference.

The tip electrode 36 has a fluid passage 35 and first and second blind holes 31 and 33 that extend longitudinally from the cavity 72. Similar to the embodiment of FIGS. 3A, 3B and 4, a hollow tube 38 is provided in the fluid passage 35 and hollow cups 40 and 42 are provided in the blind holes 31 and 33. The second fluid tube segment 48, puller wire 50, thermocouple wires 41 and 43, and tip electrode lead wire 44 are mounted in the tip electrode in a manner similar to that described above with respect to FIGS. 3A, 3B and 4. The electromagnetic sensor 64 is connected to a electromagnetic sensor cable 65, which extends through the third lumen 34 of the tip section 14, through the central lumen 18 of the catheter body 12, and into the control handle 16. The electromagnetic sensor cable 65 then extends out the proximal end of the control handle 16 within an umbilical cord (not shown) to a sensor control module (not shown) that houses a circuit board (not shown). Alternatively, the circuit board can be housed within the control handle 16, for example, as described in U.S. patent application Se. No. 08/924,616, entitled "Steerable Direct Myocardial Revascularization Catheter", the disclosure of which is incorporated herein by reference. The electromagnetic sensor cable comprises multiple wires encased within a plastic covered sheath. In the sensor control module, the wires of the electromagnetic sensor cable are connected to the circuit board. The circuit board amplifies the signal received from the electromagnetic sensor and transmits it to a computer in a form understandable by the computer by means of the sensor connector at the proximal end of the sensor control module. Also, because the catheter is designed for single use only, the circuit board preferably contains an EPROM chip which shuts down the circuit board approximately 24 hours after the catheter has been used. This prevents the catheter, or at least the electromagnetic sensor, from being used twice. Suitable electromagnetic sensor for use with the present invention are described, for example, in U.S. Pat. Nos. 5,558,091, 5,443,489, 5,480,422, 5,546,951, 5,568,809, and 5,391,199 and International Publication No. WO 95/02995, the disclosures of which are incorporated herein by reference. A preferred electromagnetic mapping sensor 72 has a length of from about 6 mm to about 7 mm and a diameter of about 1.3 mm.

The catheter body 12 is generally similar to that described above, having an open central lumen 18. Preferably, the catheter body 12 in this embodiment does not comprise a stiffening tube 20, however, because additional space is needed within the central lumen 10 to include the electromagnetic sensor cable sensor cable. The catheter body has an outer diameter preferably no greater than about 8 French, more preferably about 7 to about 7.5 French, and if desired, no greater than about 5 french.

Other similar tip electrode designs can also be provided. For example, as shown in FIGS. 10 to 13, the tip electrode 36 may comprise a body 76 and an insert 78, similar to the embodiment of FIGS. 6A, 6B and 7. As in that embodiment, the body 76 forms a shell at the distal end of the tip electrode 36 and is formed of a porous sintered metal material as described above. The body 76 has a cavity 80 at its proximal end into which the insert 78 fits. The insert 78 is formed of a solid metal material, also as described above. The insert 78 has a fluid passage 35 that extends longitudinally through the insert into which the second fluid tube segment (not shown) is anchored. The insert 78 also has two blind holes 31 and 33 into which the electrode lead wire (not shown), thermocouple wires (not shown), and puller wire (not shown) are anchored.

However, the insert 78, rather than having a cylindrical shape, has a series of flat recessed surfaces 82 about its circumference. In the depicted embodiment, the insert 78 has three recessed surfaces 82 about the cylindrical side surface of the insert. Thus, gaps are formed between the recessed surfaces 82 of the insert 78 and the inner surface of the body 76 when the insert is mounted in the cavity of the body. Preferably the recessed surfaces 82 extend to about the distal end of the insert 78 but not all the way to the proximal end of the insert. When the insert 78 is mounted in the body 76, it is preferred that the distal end of the insert is not in flush abutting contact with against the inner surface of the body so that the gaps are in fluid communication with the distal end of the fluid passage 35. In practice, fluid passes through the fluid passage 35, over the distal end of the insert 78, into the open space formed by the recessed surfaces 82 then out the sides and distal end of the porous sintered material of the shell-shaped body 76. The proximal ends of the recessed surfaces 82 are selected to prevent fluid from exiting out the proximal end of the tip electrode 36. This design provides better distribution of the fluid throughout the sintered material of the shell-shaped body. As would be recognized, the number and shape of the recesses 82 can vary as desired. Also, the insert 78 can have any suitable shape other than cylindrical, e.g., rectangular. As would be recognized by one skilled in the art, the body 76 does not necessarily have to be in the form of a shell, i.e., with a cylindrical sidewall having a uniform thickness.

In another embodiment, the insert 78 comprises a relatively thin, preferably disc-shaped, proximal plate 84 having a proximal surface and a distal surface and three holes 86, 88 and 90 extending therethrough. Preferably, the first hole 86 is larger than the second hole 88 and third hole 90. Attached to and extending distally from the distal surface of the proximal plate 84 are a hollow tube 92 and two hollow cups 94 and 96. The interior of the hollow tube 92 forms a passage 98 that is in communication with the first hole 86, and the interiors (not shown) of the first and second hollow cups 94 and 96 are in communication with the second hole 88 and third hole 90. The entire insert 78 is made of a non-porous, preferably solid metal, material, as described above. The second fluid tube segment (not shown) extends into the proximal end of the hollow tube 92, as described above, for passage of fluid through the interior of the hollow tube and out its distal end. The hollow cups 94 and 96 are open at their proximal ends and closed at their distal ends. The electrode lead wire (not shown), thermocouple wires (not shown), and puller wire (not shown) are anchored in the hollow cups 94 and 96, as described above. This insert 78 is preferably combined with a shell-shaped body 76 having a generally open interior region 100. Accordingly, fluid that passes through passage 98 enters the open interior region 100 of the body. The proximal plate 84 prevents the fluid from flowing out the proximal end of the open interior region 100. This design increases the distribution of fluid along the inside surface of the porous body, which increases the uniformity of the distribution on the outside surface of the body.

Figure 19:
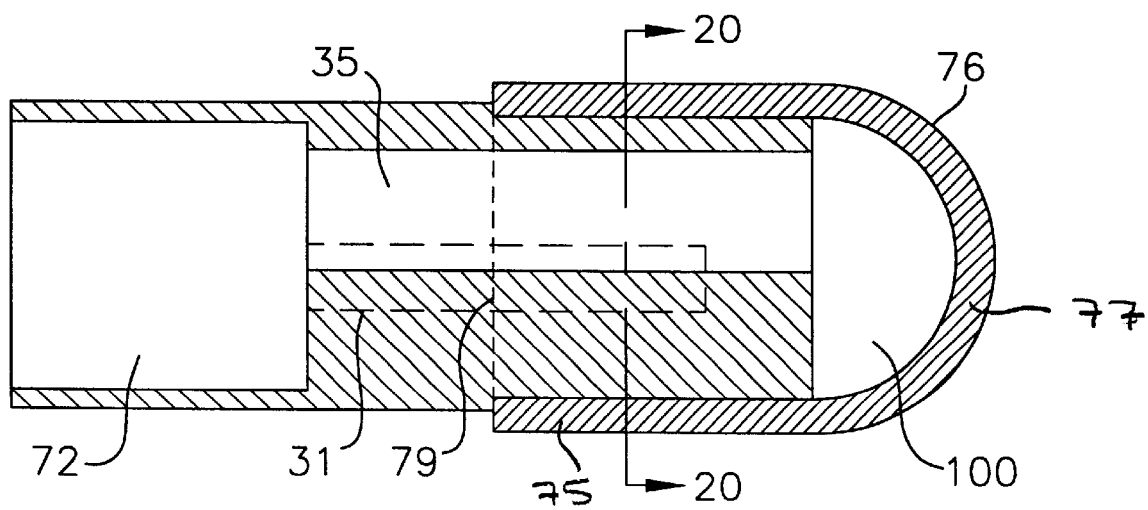
FIG. 19 is a side cross-sectional view of another alternative tip electrode according to the invention.
Figure 20:
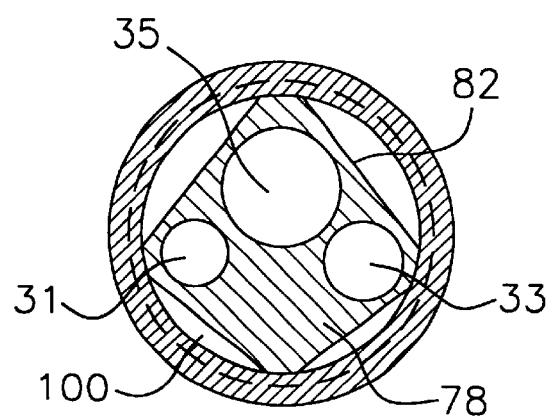
FIG. 20 is a longitudinal cross-sectional view of the tip electrode of FIG. 19.

Another alternative embodiment of a tip electrode is shown in FIGS. 19 and 20. This tip electrode is particularly useful for a catheter having an electromagnetic sensor, for example, as an alternative to the electrode depicted in FIG. 9 and described above. The electrode comprises a shell-shaped body 76, i.e.,generally cup-shaped with an open interior region 100 and an open proximal end and a cylindrical sidewall 75 having a uniform thickness, as in the embodiment discussed above, and an insert 78. The body 76 is made of a porous material, as described above.

The insert 78 is generally cylindrical and comprises a non-porous material, as described above. The insert 78 comprises a proximal end having a diameter smaller than the diameter of the proximal end of the body 76, and a distal end having a diameter smaller than the diameter of the proximal end of the insert. The proximal end and distal end of the insert 78 meet at joint 79, which is in line with the proximal end of the body 76. A generally hollow cavity 72 is formed in the proximal end of the insert 78. An electromagnetic sensor (not shown) can be mounted partially in the cavity 72, as described above. The insert 78 comprises a fluid passage 35 and first and second blind holes 31 and 33 that extend longitudinally from the cavity 72. In the depicted embodiment, the second blind hole 33 is larger than the first blind hole 31, although the relative sizes of the blind holes can vary.

The distal end of the insert 78, rather than having a cylindrical shape, has a series of flat recessed surfaces 82 about its circumference. In the depicted embodiment, the insert 78 has four recessed surfaces 82 about the cylindrical side surface of the insert. Thus, gaps are formed between the recessed surfaces 82 of the insert 78 and the inner surface of the shell-shaped body 76 when the insert is mounted in the cavity or open interior region 100 of the body. Preferably the recessed surfaces 82 extend to about the distal end of the insert 78 but not all the way to the joint 79 between the proximal and distal ends of the insert. When the insert 78 is mounted in the body 76, it is preferred that the distal end of the insert is not in flush abutting contact with against the inner surface of the body so that the gaps are in fluid communication with the distal end of the fluid passage 35. In practice, fluid passes through the fluid passage 35, over the distal end of the insert 78, into the open space formed by the recessed surfaces 82 then out the sides and distal end of the porous sintered material of the body 76. The proximal ends of the recessed surfaces 82 are selected to prevent fluid from exiting out the proximal end of the body 76, similar to the embodiment of FIGS. 10 to 13, described above. As would be recognized, the number and shape of the recesses 82 can vary as desired.

In the above-described embodiments, the tip electrode insert is described as having three separate blind holes. As would be recognized by one skilled in the art, the insert could have a single blind hole into which all of the tubes, wires, etc. extend. However, such a design is less desirable because the thermocouple would be in direct contact with the fluid, which can result in an inaccurate temperature reading.

If desired, the catheter can be multidirectional, i.e., having two or more puller wires to enhance the ability to manipulate the tip section in more than one direction or to form two or more different curves. A description of such a design is described in U.S. patent application Ser. Nos. 08/924,611 (filed Sep. 5, 1997), 09/130,359 (filed Aug. 7, 1998), 09/134,009 (filed Aug. 14, 1998), 09/143,426 (filed Aug. 28, 1998), 09/205,631 (filed Dec. 3, 1998), and 09/274,050 (filed Mar. 22, 1999), the disclosures of which is incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A porous tip electrode for a catheter, the electrode comprising:

a body, having proximal and distal ends, comprising a porous material through which fluid can pass and having a cavity therein; and an insert comprising a non-porous metal material contained within the cavity and having at least one passage extending therethrough.

2. An electrode according to claim 1, wherein the cavity extends from the proximal end of the body.

3. An electrode according to claim 1, wherein the distal end of the passage is in contact with the body.

4. An electrode according to claim 1, wherein the passage comprises at least one transverse branch.

5. An electrode according to claim 1, wherein the body is in the form of a shell having a radius, a cylindrical sidewall, an open interior and a hemispherical cap at its distal end.

6. An electrode according to claim 5, wherein the cylindrical sidewall has a uniform thickness.

7. An electrode according to claim 6, wherein the cylindrical sidewall has a thickness equal to less than about 50% of the radius of the shell.

8. An electrode according to claim 6, wherein the cylindrical sidewall has a thickness equal to less than about 30% of the radius of the shell.

9. An electrode according to claim 6, wherein the hemispherical cap has a uniform thickness approximately equal to the thickness of the cylindrical sidewall.

10. An electrode according to claim 5, wherein the insert is generally cylindrical having a distal end surface, a proximal end surface, and a cylindrical side surface.

11. An electrode according to claim 10, wherein the cylindrical side surface of the insert has at least one recessed surface portion, thereby creating a gap between the insert and the body, the gap being in fluid communication with the distal end of the passage.

12. An electrode according to claim 5, wherein the insert comprises:

a proximal plate having a proximal surface and a distal surface and at least one hole extending through the proximal portion from its proximal surface to its distal surface;

a hollow tube attached to and extending distally from the distal surface of the proximal plate, the hollow interior of the tube forming a passage in communication with the hole.

13. An electrode according to claim 12, wherein the proximal plate is disc-shaped.

14. An electrode according to claim 5, wherein the insert comprises:

a proximal plate having a proximal surface and a distal surface and three holes extending therethrough;

a hollow tube attached to and extending distally from the distal surface of the proximal plate having a passage in communication with one hole;

two hollow cups attached to the distal surface of the proximal plate, each having an internal region in communication with a corresponding hole.

15. An electrode according to claim 14, wherein the proximal plate is disc-shaped.

16. An electrode according to claim 1, wherein the body comprises a recessed stem at its proximal end.

17. An electrode according to claim 1, wherein the body has a proximal end and a distal end, wherein the proximal end is formed of a non-porous material and the distal end is formed of a porous material.

18. An electrode according to claim 1, wherein the insert comprises:
   a proximal plate having a proximal surface and a distal surface and at least one hole extending through the proximal portion from its proximal surface to its distal surface;
   a hollow tube attached to and extending distally from the distal surface of the proximal plate, the hollow interior of the tube forming a passage in communication with the hole.

19. An electrode according to claim 18, wherein the proximal plate is disc-shaped.

20. An electrode according to claim 18, wherein the body has a generally open interior region.

21. An electrode according to claim 1, wherein the insert comprises:
   a proximal plate having a proximal surface and a distal surface and three holes extending therethrough;
   a hollow tube attached to and extending distally from the distal surface of the proximal plate having a passage in communication with one hole;
   two hollow cups attached to the distal surface of the proximal plate, each having an internal region in communication with a corresponding hole.

22. An electrode according to claim 21, wherein the proximal plate is disc-shaped.

23. An electrode according to claim 21, wherein the shell has a generally open interior region.

24. An electrode according to claim 1, wherein the porous material comprises sintered metal particles.

25. An electrode according to claim 24, wherein the metal particles are generally irregularly-shaped.

26. An electrode according to claim 24, wherein the metal particles are generally rounded.

27. An electrode according to claim 24, wherein the metal particles are generally spherical.

28. An electrode according to claim 24, wherein the metal particles comprise small particles and large particles, wherein the large particles have a mean diameter at least about 2.5 times greater than the mean diameter of the small particles.

29. An electrode according to claim 28, wherein the large particles have a mean diameter at least about 4 times greater than the mean diameter of the small particles.

30. An irrigated tip catheter comprising:
   a catheter body having an outer wall, proximal and distal ends, and a lumen extending therethrough;
   a tip section comprising a segment of flexible tubing having proximal and distal ends and at least one lumen therethrough, the proximal end of the tip section being fixedly attached to the distal end of the catheter body;
   a porous tip electrode fixedly attached to the distal end of the tubing of the tip section, the tip electrode having an outer surface and comprising:
      a body, having proximal and distal ends, comprising a porous material through which fluid can pass and having a cavity therein; and
      an insert comprising a non-porous metal material contained within the cavity and having at least one passage extending therethrough and in fluid communication with a lumen in the tip section;
   an infusion tube having proximal and distal ends, said infusion tube extending through the central lumen in the catheter body, wherein the distal end of the infusion tube is in fluid communication with the proximal end of the passage in the tip electrode, whereby fluid can flow through the infusion tube, into the passage in the tip electrode and through the porous material of tip electrode to the outer surface of the tip electrode.

31. A catheter according to claim 30, wherein the distal end of the infusion tube extends into and is fluid communication with a lumen in the tip section that is in fluid communication with the passage in the tip electrode, whereby fluid can flow from the infusion tube, through the tip lumen, through the passage, through the porous material of the tip electrode, and to the outer surface of the tip electrode.

32. A catheter according to claim 30, wherein the body is in the form of a shell having a radius, a cylindrical sidewall, an open interior and a hemispherical cap at its distal end.

33. A catheter according to claim 30, wherein the cylindrical sidewall has a uniform thickness.

34. A catheter according to claim 33, wherein the cylindrical sidewall has a thickness equal to less than about 50% of the radius of the shell.

35. A catheter according to claim 33, wherein the cylindrical sidewall has a thickness equal to less than about 30% of the radius of the shell.

36. A catheter according to claim 33, wherein the hemispherical cap has a uniform thickness approximately equal to the thickness of the cylindrical sidewall.

37. A catheter according to claim 32, wherein the insert is generally cylindrical having a distal end surface, a proximal end surface, and a cylindrical side surface.

38. A catheter according to claim 37, wherein the cylindrical side surface of the insert has at least one recessed surface portion, thereby creating a gap between the insert and the body, the gap being in fluid communication with the distal end of the passage.

39. An electrode according to claim 1, wherein the insert is contained in part within the cavity.

40. An electrode according to claim 1, wherein the insert is contained entirely within the cavity.

41. An electrode according to claim 1, wherein the insert has a distal end that is located proximal to the distal end of the body.

* * * * *

UNITED STATES PATENT AND TRADEMARK OFFICE
CERTIFICATE OF CORRECTION

PATENT NO. : 6,466,818 B1
DATED : October 15, 2002
INVENTOR(S) : Moaddeb et al.

It is certified that error appears in the above-identified patent and that said Letters Patent is hereby corrected as shown below:

Column 17,
Line 8, after "surface;", insert -- and --.
Line 23, after "with one hole;", insert -- and --.

Column 18,
Lines 18-19, delete "is fluid communication", insert -- is in fluid communication --.

Signed and Sealed this

Sixth Day of September, 2005

JON W. DUDAS
*Director of the United States Patent and Trademark Office*